(12) United States Patent
Rashman

(10) Patent No.: US 6,223,440 B1
(45) Date of Patent: *May 1, 2001

(54) AUTOCLAVABLE STAINLESS STEEL MEDICAL INSTRUMENTS WITH POLYPROPYLENE INJECTED COLOR HANDLES

(76) Inventor: Richard Rashman, 3630 S. Sepulveda Blvd., #144, Los Angeles, CA (US) 90034

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 565 days.

(21) Appl. No.: 08/410,852

(22) Filed: Mar. 27, 1995

(51) Int. Cl.$^7$ .................... B26B 3/00; B26B 13/02
(52) U.S. Cl. .................... 30/340; 30/232; 30/341; 606/167; 606/205
(58) Field of Search .................... 30/232, 254, 340, 30/85, 123, 341; 81/DIG. 5, 121.1; 606/205–207, 174, 167, 166, 175, 208, 209, 138, 1

(56) References Cited

U.S. PATENT DOCUMENTS

| | | | | |
|---|---|---|---|---|
| 1,984,839 | * | 12/1934 | Murray | 81/DIG. 5 |
| 3,537,967 | * | 11/1970 | Kelley et al. | 606/205 |
| 3,740,779 | * | 6/1973 | Rubricuis . | |
| 3,750,282 | * | 8/1973 | Eaton et al. | 30/254 |
| 4,671,916 | * | 6/1987 | Hamas | 606/174 |
| 4,798,000 | * | 1/1989 | Bedner et al. | 606/174 |
| 4,882,867 | * | 11/1989 | Linden | 40/625 |
| 5,573,529 | * | 11/1996 | Haak et al. | 606/1 |

* cited by examiner

*Primary Examiner*—Douglas D. Watts
(74) *Attorney, Agent, or Firm*—Blakely Sokoloff Taylor & Zafman

(57) ABSTRACT

Improved autoclavable medical instruments are manufactured with colored synthetic handles of sufficient heat resistance to allow autoclaving. This color coding assists in the segregation of instruments by ward or medical facility. The ready identification of the color-coded instruments reduces the risk of transmission of infectious diseases, as well as reducing the probability of theft or loss.

7 Claims, 1 Drawing Sheet

AUTOCLAVABLE STAINLESS STEEL MEDICAL INSTRUMENTS WITH POLYPROPYLENE INJECTED COLOR HANDLES

BACKGROUND OF THE INVENTION

1. Field of the Invention

The invention relates to autoclavable medical instruments. More specifically, it relates to making autoclavable medical instruments readily identifiable.

2. Prior Art

Autoclavable medical instruments have typically been manufactured entirely from stainless steel or another metal substantially non-degradable in body fluids. As such, all instruments of a particular type look exactly the same. Thus, it has not been possible to effectively segregate the instruments by department, or even by medical facility. Further, it is difficult, if not impossible, to distinguish personally-owned medical instruments belonging to various staff workers in any given medical facility from those owned by the facility or any other staff member.

This difficulty leads to increased loss and theft which escalate medical costs since cost of theft and loss is inherently absorbed into the overhead of any medical facility. More importantly, inability to segregate by ward increases a risk of transmission of infectious diseases because instruments may inadvertently be moved from an infectious ward to a non-infectious ward and through error, adequate sterilization procedures may not have been performed. If the instruments were, at a glance, identifiable with a specific ward or facility, the incidence of loss, theft, and infectious disease transmission could be easily reduced.

Therefore, it is desirable to develop a way to make such medical instruments readily recognizable while retaining their autoclavable nature. Further, the instrument must remain substantially non-degradable under the normal conditions in which the instrument is used.

SUMMARY OF THE INVENTION

The present invention provides a way to make autoclavable medical instruments readily identifiable. By manufacturing medical instruments with synthetic colored handles, the instruments thereby become more easily identifiable. It is, thus, possible to segregate instruments by color, and therefore, by ward or medical facility. One benefit of this segregation is reduced risk of transmission of infectious diseases as instruments move between hospital wards. As the instruments are more readily identifiable, they will be less disposed to theft and loss. By selecting a synthetic material with a sufficiently high continuous heat resistance and which is non-degradable in natural body fluids, integrity and autoclavability of the instruments are assured.

DETAILED DESCRIPTION

Improved autoclavable medical instruments are disclosed. Throughout the following description, numerous details such as specific shapes and materials are set forth in order to provide a more thorough understanding of the present invention. In other instances, well-known elements and manufacturing methods are not described in detail so as not to obscure the present invention unnecessarily. Moreover, throughout the following Specification, the present invention is described primarily with reference to bandage scissors. It is to be understood that the invention is equally applicable to other medical instruments which must be autoclavable.

Figure 1:
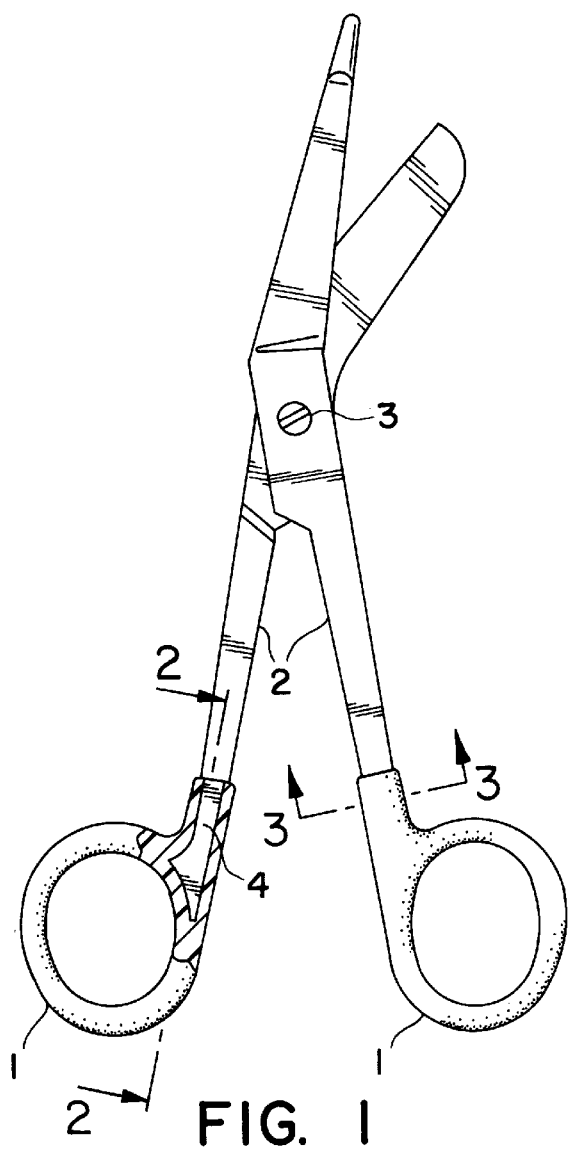
FIG. 1 is a plan view of an exemplary embodiment of the instant invention.

Referring now to FIG. 1, in one embodiment of the present invention, stainless steel scissor shanks 2 are forged with a hydraulic hammer machine providing twenty-eight tons of stroke power. The forged scissor shanks 2 are then trimmed and filed. The shanks 2 can then be heat treated and tempered using electric furnaces. The surface of the shanks can then be ground and semi-polished by hand and using an electric grinding wheel. To form the handles 1, the end of the scissor shanks 4 are inserted into a screw injection molding machine which forms the handles 1 from melted polypropylene plastic. The polypropylene must be injection grade and have sufficiently high continuous heat resistance to withstand autoclaving of the finished instrument. A continuous heat resistance of 250° F. has been found satisfactory for this purpose. The two shanks 2 are then attached using a stainless steel screw 3 and a final hand-polish yield the finished instrument. Further, once the instrument is finished, it is desirable that the synthetic handles 1 be substantially free from pores and interstices as such pores and interstices might allow contaminants to become trapped therein. It is also desirable that any interstices formed between the shaft end 4 and the handles 1 be hermetically sealed to prevent contaminant infiltration. The above-described process has been found successful in accomplishing this goal.

Figure 2:
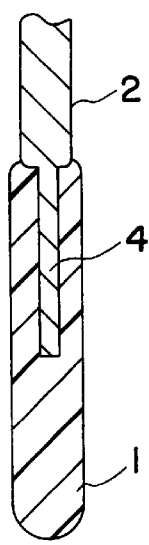
FIG. 2 is a cross-sectional view of the instant invention illustrating the interaction between the end of middle shank and the synthetic handle.
Figure 3:
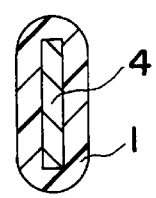
FIG. 3 is a second cross-sectional view further illustrating interaction between the shank and the handle in the instant invention.

FIGS. 2 and 3 are cross-sectional views showing how the synthetic handle 1 envelops the end of the shank 4 in the finished instrument.

Figure 4:
FIG. 4 is a plan view of an alternative embodiment of the instant invention.
Figure 5:
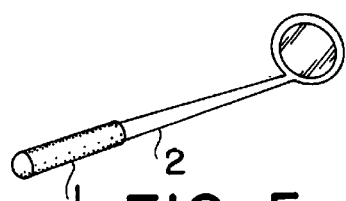
FIG. 5 is a perspective view of a second alternative embodiment of the instant invention.
Figure 6:
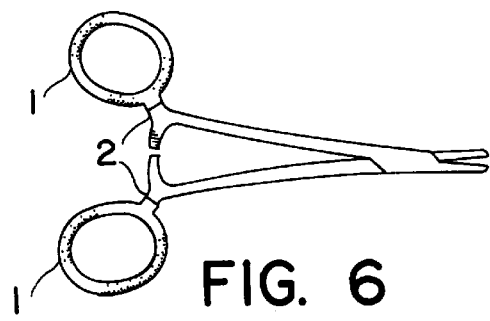
FIG. 6 is a plan view of a third alternative embodiment of the instant invention.
Figure 7:
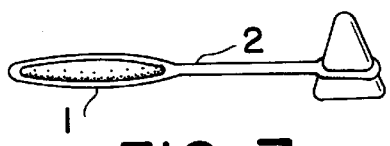
FIG. 7 is a plan view of a fourth alternative embodiment of the instant invention.

Referring now to FIGS. 4–7, showing other medical instruments with synthetic handles 1 molded onto metal shafts 2 such that the end 4 is enveloped by the synthetic material. FIG. 4 shows a scalpel, FIG. 5 a probe, FIG. 6 a hemostat, and FIG. 7 a reflex hammer.

Significantly, the polypropylene handles 1 can be formed in a multitude of colors, thus, allowing color coding of the scissors which facilitates segregation by ward. Additionally, the described handles are autoclavable as well as non-degradable in normal body fluids. Both qualities are essential to surgical instruments and highly desirable in all medical instruments. It will be recognized by those of ordinary skill in the art that other synthetic materials with the ready colorability, the necessary heat resistance, and which are non-degradable in body fluids could be used to form the handle and such other materials are within the scope and contemplation of the invention.

It will be recognized by one of ordinary skill in the art that the invention is applicable to all autoclavable medical instruments, not just those depicted in the figures. As such, other medical instruments are within the scope and contemplation of the invention. The description herein is by way of illustration, not by way of limitation, and will be recognized that the above-described invention may invite other specific forms without departing from the spirit or central characteristics of the disclosure. Thus, the invention should only be limited as set forth in the appended claims.

What is claimed is:

1. An autoclavable medical instrument comprising:
    a metallic shaft having an end; and
    a colored synthetic handle molded to encase the end of the metallic shaft wherein the color of the synthetic handle identifies the instrument as belonging to a predetermined group.

2. The autoclavable medical instrument of claim 1 wherein the metallic shaft and the synthetic handle are substantially non-degradable in body fluids.

3. The autoclavable medical instrument of claim 2 wherein the synthetic handle is substantially non-porous and defines substantially no interstices with the shaft.

4. A method of making a medical instrument readily identifiable comprising the steps of
    producing a metal portion of the instrument having a shaft; and
    encapsulating an end of the shaft in a colored autoclavable synthetic material such that the encapsulating synthetic material identifies the medical instrument as belonging to a predetermined group.

5. The method of claim 4 wherein the handle is substantially non-degradable in body fluids.

6. The method of claim 4 wherein the synthetic material and the shaft define substantially no interstices.

7. The method of claim 4 further comprising the step of molding the synthetic material into a functional handle.

* * * * *